(12) United States Patent
Mishra

(10) Patent No.: US 9,643,007 B2
(45) Date of Patent: May 9, 2017

(54) UTILIZATION OF DIFFERENT LOUDNESS ENCODING SCHEMES IN COCHLEAR IMPLANT SYSTEMS

(71) Applicants: ADVANCED BIONICS AG, Staefa (CH); Lakshmi N. Mishra, Valencia, CA (US)

(72) Inventor: Lakshmi N. Mishra, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,024

(22) PCT Filed: Oct. 30, 2013

(86) PCT No.: PCT/US2013/067632
§ 371 (c)(1),
(2) Date: Mar. 22, 2016

(87) PCT Pub. No.: WO2015/065401
PCT Pub. Date: May 7, 2015

(65) Prior Publication Data
US 2016/0235985 A1    Aug. 18, 2016

(51) Int. Cl.
*A61N 1/36* (2006.01)
(52) U.S. Cl.
CPC ..... *A61N 1/36032* (2013.01); *A61N 1/36189* (2013.01)
(58) Field of Classification Search
None
See application file for complete search history.

(56) References Cited

U.S. PATENT DOCUMENTS 6,249,704 B1    6/2001    Maltan et al.
6,443,891 B1    9/2002    Grevious
(Continued)

FOREIGN PATENT DOCUMENTS

WO    WO 2009/143553    12/2009

OTHER PUBLICATIONS

McKay, et al., "A practical method of predicting the loudness of complex electrical stimuli", *J. Acoust. Soc. Am.* vol. 113, No. 4, Pt. 1, Apr. 2003, Department of Otolaryngology, The University of Melbourne, 384-388 Albert Street, East Melbourne 3002, Australia. Received Jun. 14, 2002; revised Dec. 13, 2002; accepted Jan. 13, 2003.

(Continued)

*Primary Examiner* — Brian T Gedeon
(74) *Attorney, Agent, or Firm* — ALG Intellectual Property, LLC

(57) ABSTRACT

An exemplary sound processor included in a cochlear implant system associated with a patient may 1) identify a loudness level of an audio signal presented to the patient, 2) determine that a stimulation pulse amplitude corresponding to the loudness level is greater than a maximum stimulation pulse amplitude allowed by a compliance voltage associated with a cochlear implant implanted within the patient, and 3) direct, in response to the determination that the stimulation pulse amplitude is greater than a maximum stimulation pulse amplitude allowed by the compliance voltage, the cochlear implant to represent the loudness level to the patient by directing the cochlear implant to generate and apply one or more stimulation pulses to the patient in accordance with at least one of a first encoding scheme that includes pulse density modulation and a second encoding scheme that includes a combination of pulse amplitude modulation and pulse width modulation.

20 Claims, 7 Drawing Sheets

(56) References Cited

U.S. PATENT DOCUMENTS

| | | |
|---|---|---|
| 7,317,944 B1 | 1/2008 | Overstreet |
| 8,130,991 B2 | 3/2012 | Rasmussen et al. |
| 8,229,148 B2 | 7/2012 | Rasmussen et al. |
| 8,351,628 B2 | 1/2013 | Ochoco et al. |
| 9,539,430 B2 * | 1/2017 | Mishra et al. ..... A61N 1/36032 |
| 2003/0167077 A1 | 9/2003 | Blamey et al. |
| 2007/0043403 A1 | 2/2007 | Blamey et al. |
| 2007/0135868 A1 | 6/2007 | Shi et al. |
| 2009/0125082 A1 | 5/2009 | Schleich |
| 2012/0022613 A1 | 1/2012 | Meskens |
| 2013/0023964 A1 | 1/2013 | Stafford et al. |
| 2013/0103111 A1 | 4/2013 | Meskens |

OTHER PUBLICATIONS

Chatterjee, "Effects of stimulation mode on threshold and loudness growth in multielectrode cochlear implants", *J. Acoust. Soc. Am.* 105 (2), Pt. 1, Feb. 1999.

International Search Report and Written Opinion received in International Application No. PCT/US13/067632, dated Jan. 31, 2014.

* cited by examiner

UTILIZATION OF DIFFERENT LOUDNESS ENCODING SCHEMES IN COCHLEAR IMPLANT SYSTEMS

BACKGROUND INFORMATION

Cochlear implant systems typically use pulse amplitude modulation to encode loudness. In other words, a loudness level of an audio signal presented to a cochlear implant patient may be represented to the patient by modulating (e.g., setting) an amplitude of a stimulation pulse that is applied to the patient (e.g., by way of an intracochlear electrode). To illustrate, a cochlear implant system may represent a relatively low loudness level by applying a stimulation pulse that has a relatively low amplitude and a relatively high loudness level by applying a stimulation pulse that has a relatively high amplitude.

The maximum amplitude that any given stimulation pulse may have is governed by the compliance voltage associated with a cochlear implant included within the cochlear implant system. For example, if the compliance voltage is represented by V and the impedance of the tissue associated with an electrode is represented by R, the maximum current (represented by $I_{max}$) that may be applied by way of the electrode is defined by Ohm's law in the following equation: $I_{max}=V/R$.

Unfortunately, conventional cochlear implant systems cannot adjust the compliance voltage in an instantaneous manner to guarantee efficacy of stimulation while minimizing power consumption. In other words, with pulse amplitude modulation, the compliance voltage is typically set to achieve the largest stimulation pulse amplitude in a window of time (e.g., a stimulation frame) as opposed being dynamically adjusted during the window of time to match the amplitudes of individual stimulation pulses. This may result in power consumption inefficiencies, which, in turn, may adversely require a relatively large power source (e.g., battery).

Pulse width modulation has been proposed as a potential alternative to pulse amplitude modulation. Pulse width modulation offers the advantage of minimizing losses due to compliance voltage mismatch between what is required and what is maintained. However, pulse width modulation is difficult to implement and may suffer from limited dynamic range and resolution issues. For example, the relationship between loudness and charge delivered using pulse width modulation may not have a large enough dynamic range for pulse width modulation to be efficacious.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
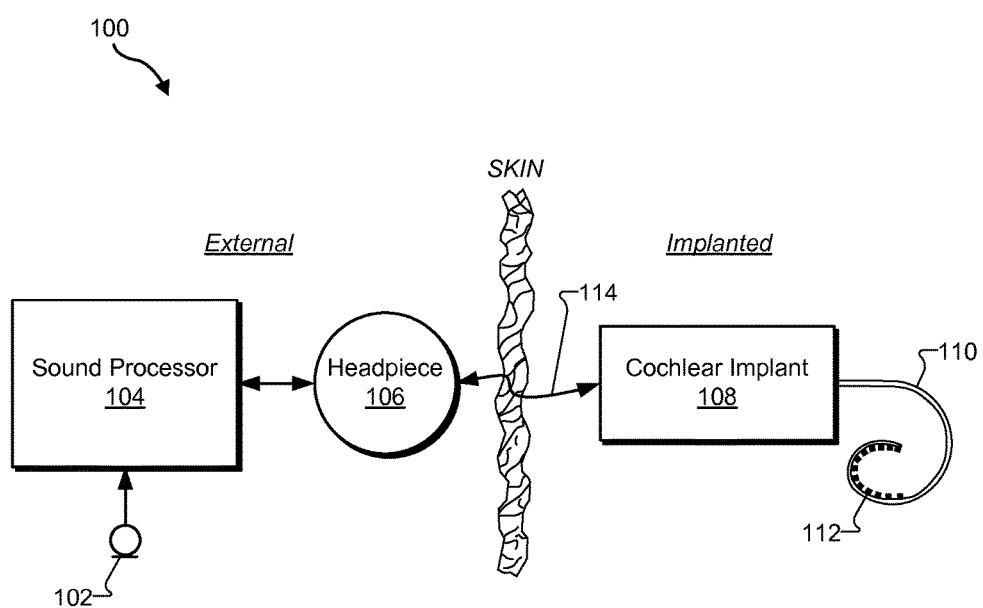
FIG. 1 illustrates an exemplary cochlear implant system according to principles described herein.

Systems and methods that facilitate utilization of different loudness encoding schemes (also referred to as "encoding schemes") in a cochlear implant system are described herein. In some examples, as will be described below, a cochlear implant system may dynamically switch between different loudness encoding schemes (e.g., during the same time window or stimulation frame) in order to accommodate varying loudness levels of an audio signal being presented to a cochlear implant patient. In this manner, as will be illustrated below, the compliance voltage associated with the cochlear implant system may be minimized (e.g., set to a relatively low level) compared to that which would be required if only a pulse amplitude modulation scheme is utilized to encode loudness. This may facilitate increased battery life, improved performance, and/or other benefits compared to conventional loudness encoding schemes.

By way of example, a sound processor included in a cochlear implant system associated with a patient may 1) identify a loudness level of an audio signal presented to the patient, 2) determine that a stimulation pulse amplitude corresponding to the loudness level is greater than a maximum stimulation pulse amplitude allowed by a compliance voltage associated with a cochlear implant implanted within the patient, and 3) direct, in response to the determination that the stimulation pulse amplitude is greater than a maximum stimulation pulse amplitude allowed by the compliance voltage, the cochlear implant to represent the loudness level to the patient by directing the cochlear implant to generate and apply a plurality of stimulation pulses to the patient in accordance with a pulse density modulation encoding scheme.

As another example, a sound processor included in a cochlear implant system associated with a patient may 1) identify, during a first time slot, a first loudness level of an audio signal presented to the patient, 2) determine that a first stimulation pulse amplitude corresponding to the first loudness level is less than or equal to a maximum stimulation pulse amplitude allowed by a compliance voltage associated with a cochlear implant implanted within the patient, 3) direct, in response to the determination that the first stimulation pulse amplitude is less than or equal to the maximum stimulation pulse amplitude applied by the compliance voltage, the cochlear implant to represent the first loudness level to the patient by directing the cochlear implant to generate and apply a single stimulation pulse that has the first stimulation pulse amplitude to the patient in accordance with a pulse amplitude modulation encoding scheme, 4) identify, during a second time slot subsequent to the first time slot, second first loudness level of the audio signal presented to the patient, 5) determine that a second stimulation pulse amplitude corresponding to the second loudness level is greater than the maximum stimulation pulse amplitude allowed by the compliance voltage, and 6) direct, in response to the determination that the second stimulation pulse amplitude is greater than the maximum stimulation pulse amplitude applied by the compliance voltage, the cochlear implant to represent the second loudness level to the patient by directing the cochlear implant to generate and apply one or more stimulation pulses in accordance with an encoding scheme that is different than the pulse amplitude modulation encoding scheme. For example, the different encoding scheme may include a pulse density modulation encoding scheme and/or an encoding scheme that includes both pulse amplitude modulation and pulse width modulation.

As used herein, a "pulse amplitude modulation encoding scheme" refers to a scheme in which pulse amplitude modulation is used to encode a loudness level of an audio signal presented to a cochlear implant patient. In pulse amplitude modulation, the amplitude (also referred to herein as the "stimulation pulse amplitude") of a stimulation pulse representative of the audio signal is modulated or adjusted to represent or convey the loudness level to the patient. An exemplary pulse amplitude modulation encoding scheme will be described in more detail below.

As used herein, a "pulse density modulation encoding scheme" refers to a scheme in which pulse density modulation is used to encode a loudness level of an audio signal presented to a cochlear implant patient. In pulse density modulation, a plurality of stimulation pulses (e.g., two stimulation pulses) are sequentially applied (e.g., in rapid succession) to a patient in order to represent or convey the loudness level to the patient. As will be described below, the combined amplitudes of the stimulation pulses may result in the patient perceiving the encoded loudness level.

As will be described below, another encoding scheme that may be used in accordance with the systems and methods described herein uses both pulse amplitude modulation and pulse width modulation to encode a loudness level of an audio signal presented to a cochlear implant patient. For example, the amplitude and pulse width of a stimulation pulse may be adjusted so that a total charge of the stimulation pulse may result in the patient perceiving the encoded loudness level.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
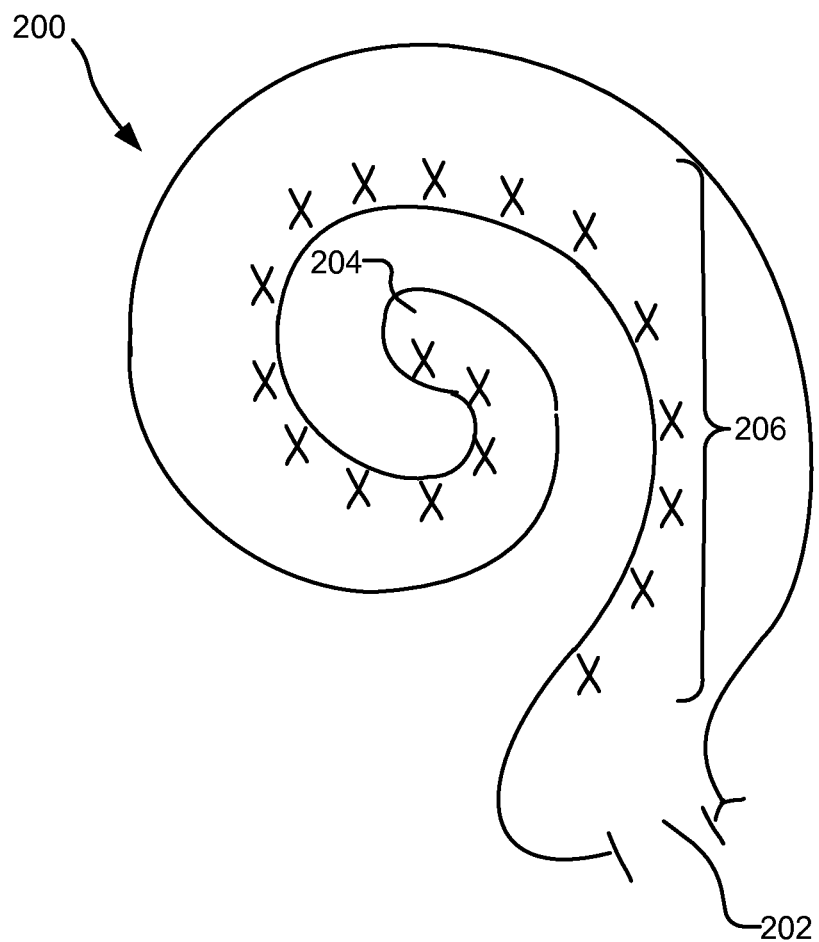
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
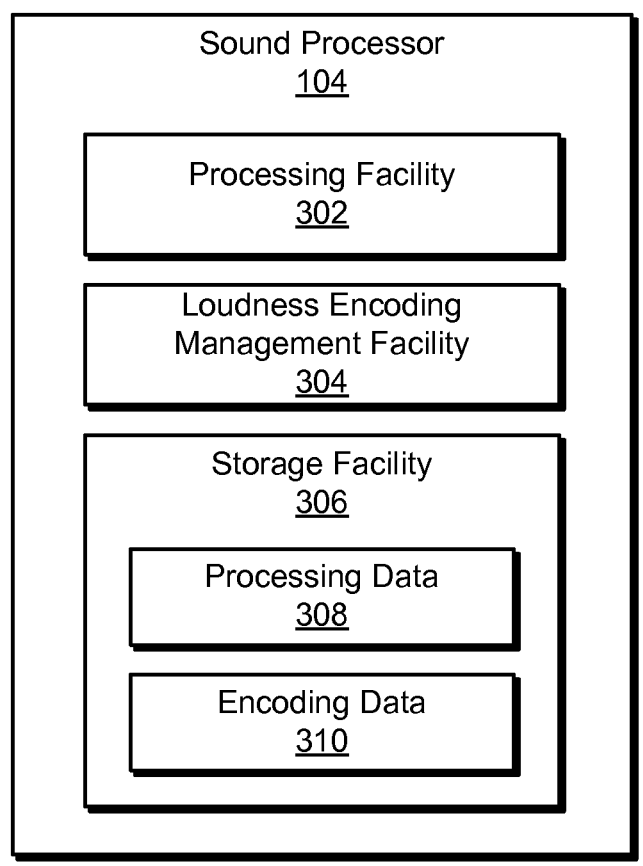
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a processing facility 302, a loudness encoding management facility 304, and a storage facility 306, which may be in communication with one another using any suitable communication technologies. Storage facility 306 may be configured to maintain processing data 308 generated and/or used by processing facility 302, and encoding data 310 generated and/or used by loudness encoding management facility 304. Storage facility 306 may maintain additional or alternative data as may serve a particular implementation. One or more of facilities 302-306 may include a computing device or processor configured to perform one or more of the functions described herein. Facilities 302-306 will now be described in more detail.

Processing facility 302 may be configured to process an audio signal presented to a cochlear implant patient (e.g., an audio signal detected by microphone 102, an audio signal input by way of an auxiliary audio input port, etc.). For example, processing facility 302 may perform one or more pre-processing operations, spectral analysis operations, noise reduction operations, mapping operations, and/or any other types of signal processing operations on a detected audio signal as may serve a particular application.

In some examples, processing facility 302 may identify a loudness level of an audio signal presented to the patient. This may be performed in any suitable manner. For example, processing facility 302 may identify a plurality of different loudness levels of an audio signal presented to the patient during a plurality of different time slots (e.g., a sequence of time slots associated with a particular window of time during which electrical stimulation representative of the audio signal is presented to the patient).

Loudness encoding management facility 304 may perform one or more loudness encoding management operations. For example, loudness encoding management facility 304 may select, based on a loudness level of an audio signal as identified by processing facility 302, a particular encoding scheme that is to be used by cochlear implant 108 to represent the loudness level to the patient. Loudness encoding management facility 304 may then direct cochlear implant 108 to generate and apply one or more stimulation pulses to the patient in accordance with the selected encoding scheme.

Loudness encoding management facility 304 may select the encoding scheme that is to be used by cochlear implant 108 to represent the loudness level to the patient in any suitable manner. For example, loudness encoding management facility 304 may first determine a maximum stimulation pulse amplitude allowed by a compliance voltage associated with cochlear implant 108. This may be performed in any suitable manner. For example, loudness encoding management facility 304 may maintain data representative of the compliance voltage as well as data representative of impedances associated with each electrode 112. Loudness encoding management facility 304 may use this data to determine the maximum stimulation pulse amplitude that may be applied by way of each electrode. For example, as described above, if the compliance voltage is represented by V and the impedance associated with an electrode is represented by R, loudness encoding management facility 304 may determine that the maximum stimulation pulse amplitude allowed by the compliance voltage for the electrode in accordance with the following equation: $I_{max}=V/R$.

Loudness encoding management facility 304 may then identify a stimulation pulse amplitude that corresponds to the identified loudness level. As used herein, a stimulation pulse amplitude that "corresponds" to an identified loudness level refers to a stimulation pulse amplitude that a single stimulation pulse must have if the single stimulation pulse is used by cochlear implant 108 to represent the loudness level to the patient in accordance with a pulse amplitude modulation encoding scheme. In this scenario, the pulse width of the single stimulation pulse is fixed as specified by data maintained by cochlear implant 108.

Loudness encoding management facility 304 may compare the stimulation pulse amplitude corresponding to the identified loudness level to the maximum stimulation pulse amplitude allowed by the compliance voltage associated with cochlear implant 108. In some examples, if the stimulation pulse amplitude corresponding to the identified loudness level is less than or equal to the maximum stimulation pulse amplitude allowed by the compliance voltage, loudness encoding management facility 304 may select a pulse amplitude modulation encoding scheme for use by cochlear implant 108 to represent the loudness level to the patient. Alternatively, if the stimulation pulse amplitude corresponding to the identified loudness level is greater than the maximum stimulation pulse amplitude allowed by the compliance voltage, loudness encoding management facility 304 may select an encoding scheme that is different than the pulse amplitude modulation encoding scheme for use by cochlear implant 108 to represent the loudness level to the patient. Various examples of this will now be provided.

Figure 4:
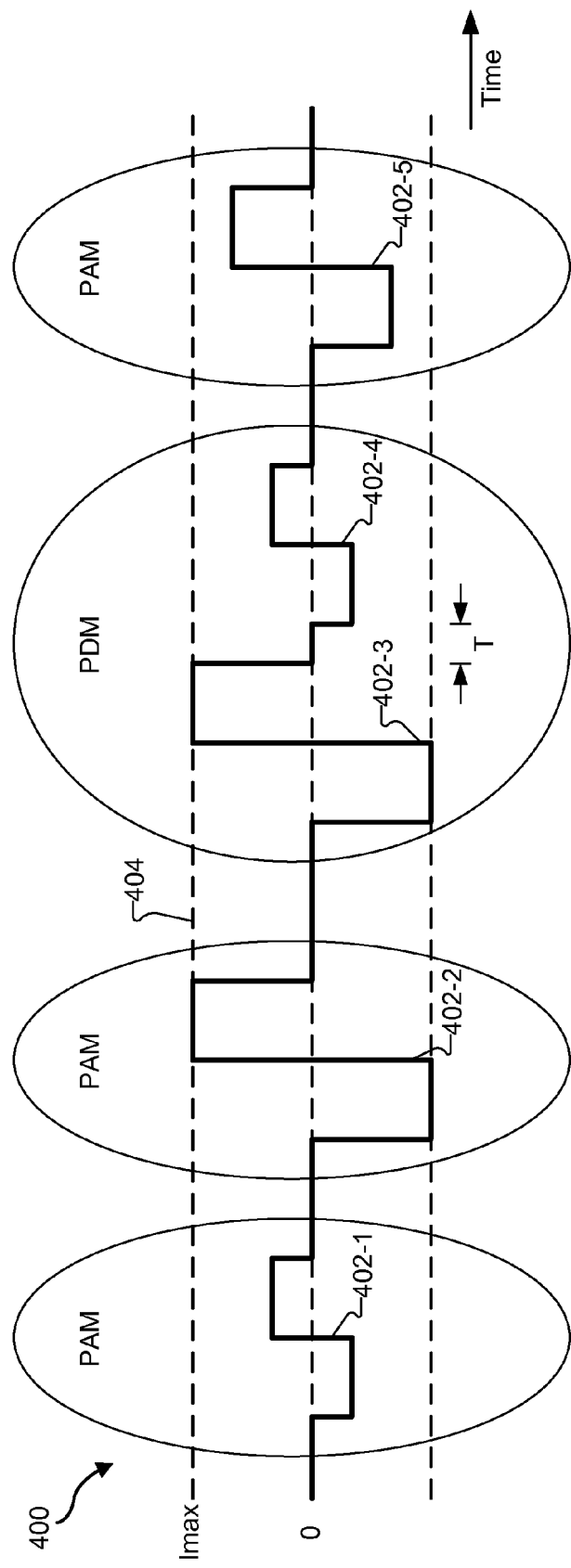
FIG. 4 illustrates an exemplary pulse train that may be generated and applied by a cochlear implant to a patient according to principles described herein.

FIG. 4 illustrates an exemplary pulse train 400 that may be applied by cochlear implant 108 by way of a particular electrode (e.g., one of electrodes 112) disposed within a patient in order to represent various loudness levels of an audio signal presented to the patient during a particular window of time (e.g., a stimulation frame). As shown, pulse train 400 may include a sequence of stimulation pulses 402 (e.g., stimulation pulses 402-1 through 402-5). As indicated, the various loudness levels may be encoded into stimulation pulses 402-1, 402-2, and 402-5 using a pulse amplitude modulation ("PAM") encoding scheme and into stimulation pulses 402-3 and 402-4 using a pulse density modulation ("PDM") encoding scheme.

To illustrate, processing facility 302 may identify, during a first time slot, a first loudness level of the audio signal presented to the patient. Loudness encoding management facility 304 may identify a first stimulation pulse amplitude that corresponds to the first loudness level and compare the first stimulation pulse amplitude to a maximum stimulation pulse amplitude allowed by the compliance voltage associated with cochlear implant 108. The maximum stimulation pulse amplitude allowed by the compliance voltage is indicated by a dotted line 404 labeled Imax in FIG. 4. In this particular example, loudness encoding management facility 304 may determine that the first stimulation pulse amplitude corresponding to the first loudness level is less than the maximum stimulation pulse amplitude allowed by the compliance voltage. In response to this determination, loudness encoding management facility 304 may direct cochlear implant 108 to represent the first loudness level to the patient by directing cochlear implant 108 to generate and apply a single stimulation pulse (i.e., stimulation pulse 402-1) that has the first stimulation pulse amplitude to the patient in accordance with a pulse amplitude modulation encoding scheme. As shown in FIG. 4, stimulation pulse 402-1 has an amplitude that is less than the maximum stimulation pulse amplitude represented by dotted line 404.

Processing facility 302 may next identify, during a second time slot that follows the first time slot, a second loudness level of the audio signal presented to the patient. Loudness encoding management facility 304 may identify a second stimulation pulse amplitude that corresponds to the second loudness level and compare the second stimulation pulse amplitude to the maximum stimulation pulse amplitude allowed by the compliance voltage associated with cochlear implant 108. In this particular example, loudness encoding management facility 304 may determine that the second stimulation pulse amplitude corresponding to the second loudness level is equal to the maximum stimulation pulse amplitude allowed by the compliance voltage. In response to this determination, loudness encoding management facility 304 may direct cochlear implant 108 to represent the second loudness level to the patient by directing cochlear implant 108 to generate and apply a single stimulation pulse (i.e., stimulation pulse 402-2) that has the second stimulation pulse amplitude to the patient in accordance with the pulse amplitude modulation encoding scheme. As shown in FIG. 4, stimulation pulse 402-2 has an amplitude that is substantially equal to the maximum stimulation pulse amplitude represented by dotted line 404.

Processing facility 302 may next identify, during a third time slot that follows the second time slot, a third loudness level of the audio signal presented to the patient. Loudness encoding management facility 304 may identify a third stimulation pulse amplitude that corresponds to the third loudness level and compare the third stimulation pulse amplitude to the maximum stimulation pulse amplitude allowed by the compliance voltage associated with cochlear implant 108. In this particular example, loudness encoding management facility 304 may determine that the third stimulation pulse amplitude corresponding to the third loudness level is greater than the maximum stimulation pulse amplitude allowed by the compliance voltage. In response to this determination, loudness encoding management facility 304 may direct cochlear implant 108 to represent the third loudness level to the patient by directing cochlear implant 108 to generate and apply two stimulation pulses (i.e., stimulation pulses 402-3 and 402-4) to the patient in accordance with a pulse density modulation encoding scheme. While two stimulation pulses 402-3 and 402-4 are shown in FIG. 4, it will be recognized that cochlear implant 108 may generate and apply more than two stimulation pulses to the patient in accordance with the pulse density modulation encoding scheme in order to represent the third loudness level to the patient.

In some examples, the sum of the amplitudes of the stimulation pulses used to encode a loudness level in accordance with a pulse density modulation encoding scheme may be substantially equal to the stimulation pulse amplitude corresponding to the loudness level. For example, in the example of FIG. 4, the sum of the amplitudes of stimulation pulses 402-3 and 402-4 may be substantially equal to the third stimulation pulse amplitude that corresponds to the third loudness level.

As shown in FIG. 4, the amplitude of stimulation pulse 402-3 is greater than the amplitude of stimulation pulse 402-4. It will be recognized that in some alternative embodiments, the first stimulation pulse applied in accordance with a pulse density modulation scheme (i.e., stimulation pulse 402-3) may have a smaller amplitude than the second stimulation pulse applied in accordance with the pulse density modulation scheme (i.e., stimulation pulse 402-4).

Loudness encoding management facility 304 may direct cochlear implant 108 to apply stimulation pulses 402-3 and 402-4 in relatively rapid succession. Because stimulation pulses 402-3 and 402-4 are applied in relatively rapid succession, the patient may perceive a loudness level corresponding to the combined amplitudes of the stimulation pulses 402-3 and 402-4. The time delay (represented in FIG. 4 as "T") that temporally separates the application of the two stimulation pulses 402-3 and 402-4 may be defined by the pulse density modulation encoding scheme. In some examples, the time delay may be based on a loudness model of electrical hearing. In some alternative examples, there is no time delay that temporally separates the application of the two stimulation pulses 402-3 and 402-4.

In some examples, loudness encoding management facility 304 may direct cochlear implant 108 to also use a pulse width modulation encoding scheme together with the pulse density modulation encoding scheme when representing the third loudness level. For example, loudness encoding management facility 304 may direct cochlear implant 108 to adjust the widths of stimulation pulses 402-3 and 402-4 in order to achieve a total charge that results in the patient perceiving the third loudness level.

Continuing with the example in FIG. 4, processing facility 302 may next identify, during a fourth time slot that follows the third time slot, a fourth loudness level of the audio signal presented to the patient. Loudness encoding management facility 304 may identify a fourth stimulation pulse amplitude that corresponds to the fourth loudness level and compare the fourth stimulation pulse amplitude to the maximum stimulation pulse amplitude allowed by the compliance voltage associated with cochlear implant 108. In this particular example, loudness encoding management facility 304 may determine that the fourth stimulation pulse amplitude corresponding to the fourth loudness level is again less than the maximum stimulation pulse amplitude allowed by the compliance voltage. In response to this determination, loudness encoding management facility 304 may direct cochlear implant 108 to represent the fourth loudness level to the patient by directing cochlear implant 108 to generate and apply a single stimulation pulse (i.e., stimulation pulse 402-5) that has the fourth stimulation pulse amplitude to the patient in accordance with the pulse amplitude modulation encoding scheme. As shown in FIG. 4, stimulation pulse 402-5 has an amplitude that is less than the maximum stimulation pulse amplitude represented by dotted line 404.

As illustrated in FIG. 4, loudness encoding management facility 304 may direct cochlear implant 108 to dynamically switch between operating in accordance with different encoding schemes (e.g., from the pulse amplitude modulation encoding scheme to the pulse density modulation encoding scheme back to the pulse amplitude modulation encoding scheme) as the pulse train 400 is applied to the patient. This direction may be performed in any suitable manner. For example, loudness encoding management facility 304 may transmit one or more control parameters (e.g., digital words) to the cochlear implant 108 that instruct cochlear implant 108 to switch between operating in accordance with the different encoding schemes. Likewise, loudness encoding management facility 304 may transmit one or more control parameters to cochlear implant 108 that instruct cochlear implant 108 how to perform the various types of encoding schemes (e.g., one or more control words that specify stimulation pulse amplitudes, stimulation pulse widths, etc.).

As illustrated in FIG. 4, by dynamically switching between different encoding schemes, loudness levels greater than that corresponding to the maximum stimulation current amplitude allowed by the compliance voltage associated with cochlear implant 108 may be achieved without increasing the compliance voltage.

In some examples, loudness encoding management facility 304 may determine that a stimulation pulse amplitude corresponding to a loudness level of an audio signal presented to the patient is greater than the maximum stimulation pulse amplitude allowed by the compliance voltage and that the loudness level cannot be represented using a pulse density modulation encoding scheme or any other encoding scheme. In other words, the loudness level may be too high to be represented in accordance with any encoding scheme while cochlear implant 108 operates at the compliance voltage. In response to this determination, loudness encoding management facility 304 may increase the compliance voltage associated with the cochlear implant 108 to a level that facilitates representation of the loudness level.

Figure 5:
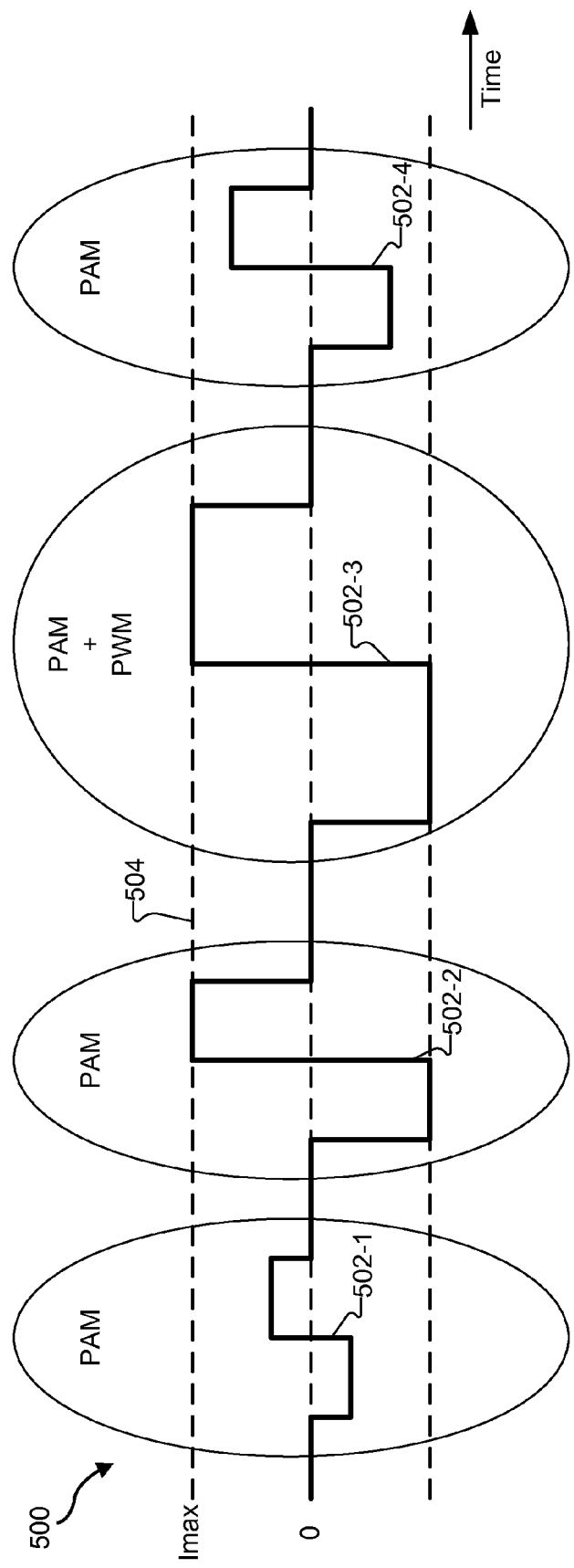
FIG. 5 illustrates another exemplary pulse train that may be generated and applied by a cochlear implant to a patient according to principles described herein.

FIG. 5 illustrates another exemplary pulse train 500 that may be applied by cochlear implant 108 by way of a particular electrode (e.g., one of electrodes 112) disposed within a patient in order to represent various loudness levels of an audio signal presented to the patient during a particular window of time (e.g., a stimulation frame). As shown, pulse train 500 may include a sequence of stimulation pulses 502 (e.g., stimulation pulses 502-1 through 502-4). As indicated, the various loudness levels may be encoded into stimulation pulses 502-1, 502-2, and 502-4 using a pulse amplitude modulation encoding scheme and into stimulation pulses 502-3 using an encoding scheme that includes both pulse amplitude modulation and pulse width modulation ("PAM+ PWM").

To illustrate, processing facility 302 may identify, during a first time slot and a second time slot subsequent to the first time slot, a first loudness level and a second loudness level of the audio signal presented to the patient. Loudness encoding management facility 304 may direct cochlear implant 108 to represent the first and second loudness levels to the patient by directing cochlear implant 108 to generate and apply stimulation pulses 502-1 and 502-2 in a similar manner as that described in connection with FIG. 4.

Processing facility 302 may next identify, during a third time slot that follows the second time slot, a third loudness level of the audio signal presented to the patient. Loudness encoding management facility 304 may identify a third stimulation pulse amplitude that corresponds to the third loudness level and compare the third stimulation pulse amplitude to the maximum stimulation pulse amplitude allowed by the compliance voltage associated with cochlear implant 108. In this particular example, loudness encoding management facility 304 may determine that the third stimulation pulse amplitude corresponding to the third loudness level is greater than the maximum stimulation pulse amplitude allowed by the compliance voltage. In response to this determination, loudness encoding management facility 304 may direct cochlear implant 108 to represent the third loudness level to the patient by directing cochlear implant 108 to generate and apply a single stimulation pulse (i.e., stimulation pulse 502-3) to the patient in accordance with an encoding scheme that includes both pulse amplitude modulation and pulse width modulation in order to represent the third loudness level to the patient. As shown, stimulation pulse 502-3 has a pulse width that is wider than the pulse widths of the stimulation pulses 502-1, 502-2 and 502-4 encoded in accordance with pulse amplitude modulation only. In this manner, a total charge of stimulation pulse 502-3 may result in the patient perceiving the third loudness level.

Figure 6:
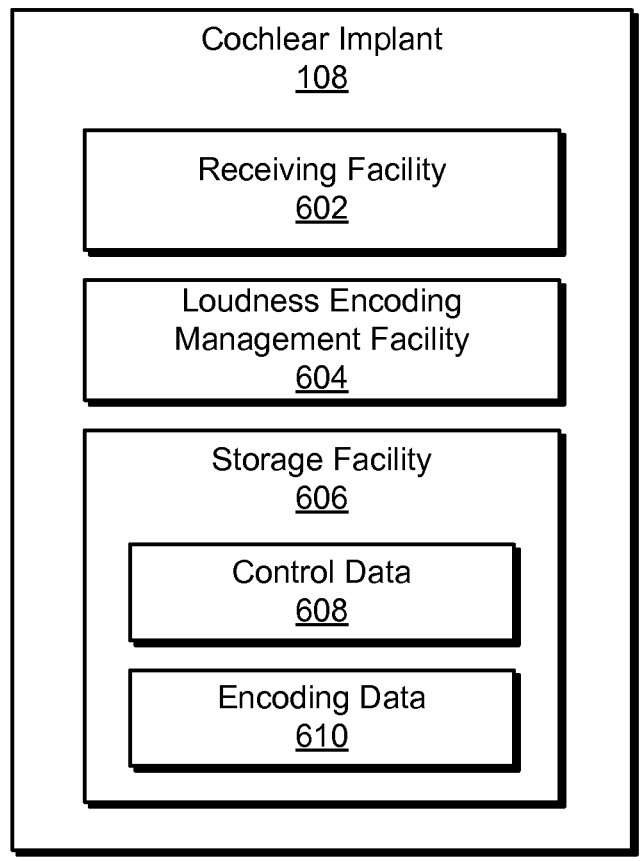
FIG. 6 illustrates exemplary components of a cochlear implant according to principles described herein.

In some alternative examples, cochlear implant 108 may perform the various loudness encoding management operations described herein. To illustrate, FIG. 6 shows components of cochlear implant 108. It will be recognized that the components shown in FIG. 6 are merely representative of the many different components that may be included in cochlear implant 108 and that cochlear implant 108 may include additional or alternative components as may serve a particular implementation.

As shown in FIG. 6, cochlear implant 108 may include a receiving facility 602, a loudness encoding management facility 604, and a storage facility 606, which may be in communication with one another using any suitable communication technologies. Storage facility 606 may be configured to maintain control data 608 received by receiving facility 602, and encoding data 610 generated and/or used by loudness encoding management facility 604. Storage facility 606 may maintain additional or alternative data as may serve a particular implementation. One or more of facilities 602-606 may include a computing device or processor configured to perform one or more of the functions described herein. Facilities 602-606 will now be described in more detail.

Receiving facility 602 may receive data (e.g., control parameters) from sound processor 104. For example, receiving facility 602 may receive an instruction from sound processor 104 for cochlear implant 108 to represent a loudness level of an audio signal to a patient.

Loudness encoding management facility 604 may perform one or more of the loudness encoding management operations described herein (e.g., one or more of the loudness encoding management operations described in connection with loudness encoding management facility 304). For example, loudness encoding management facility 604 may select, based on the loudness level indicated in the instruction received by receiving facility 602, a particular encoding scheme that is to be used by cochlear implant 108 to represent the loudness level to the patient. Loudness encoding management facility 604 may then generate and apply one or more stimulation pulses to the patient in accordance with the selected encoding scheme.

For example, receiving facility 602 may receive an instruction from sound processor 104 for cochlear implant 108 to represent a loudness level of an audio signal to a patient. Loudness encoding management facility 604 may determine that a stimulation pulse amplitude corresponding to the loudness level is greater than a maximum stimulation pulse amplitude allowed by a compliance voltage associated with the cochlear implant, and, in response, represent the loudness level to the patient by generating and applying one or more stimulation pulses to the patient in accordance with at least one of a first encoding scheme that includes pulse density modulation and a second encoding scheme that includes a combination of pulse amplitude modulation and pulse width modulation.

In some examples, a loudness level of an audio signal may be encoded in accordance with a pulse density modulation encoding scheme regardless of the amplitude of the loudness level. In other words, pulse density modulation may be used to represent all possible loudness levels of the audio signal during a particular window of time. Other characteristics of the audio signal may also be encoded in accordance with a pulse density modulation encoding scheme as may serve a particular implementation.

Figure 7:
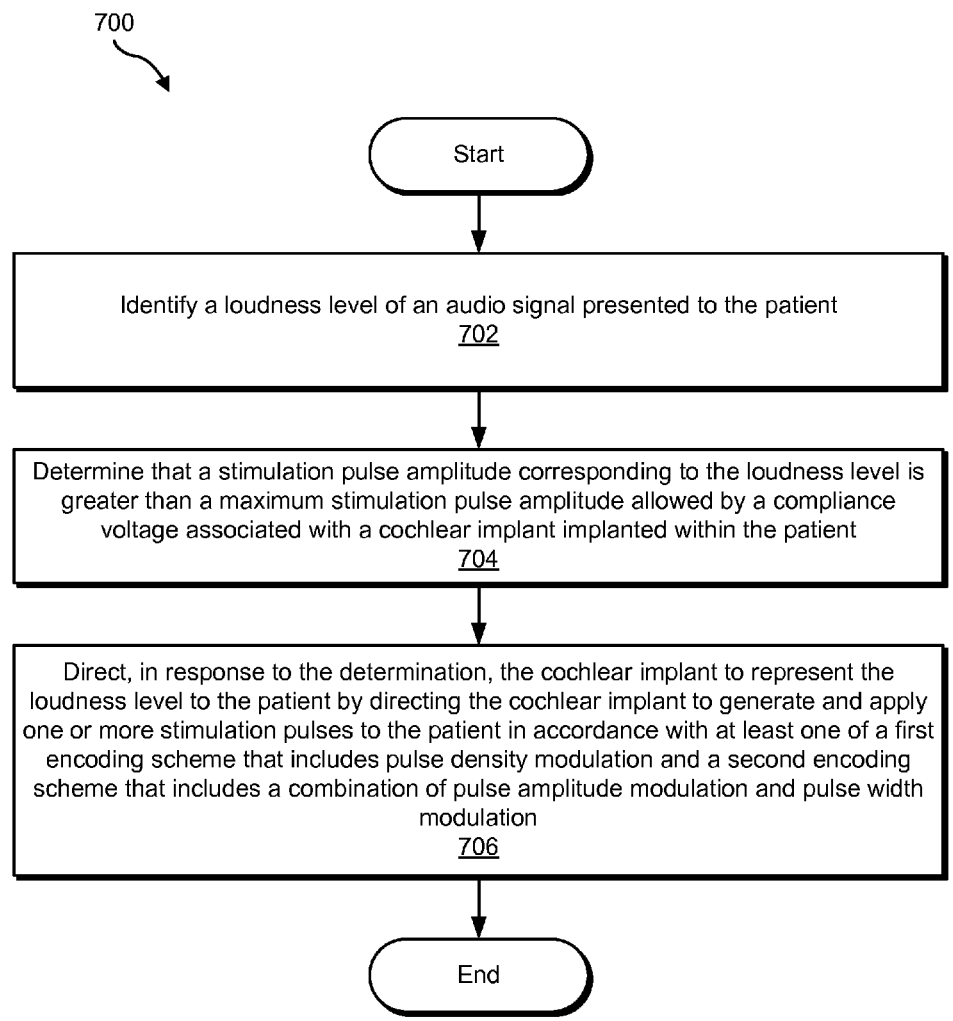
FIG. 7 illustrates an exemplary method according to principles described herein.

FIG. 7 illustrates an exemplary method 700. While FIG. 7 illustrates exemplary steps according to one embodiment, other embodiments may omit, add to, reorder, and/or modify any of the steps shown in FIG. 7. One or more of the steps shown in FIG. 7 may be performed by sound processor 104 and/or any implementation thereof.

In step 702, a sound processor identifies a loudness level of an audio signal presented to the patient. Step 702 may be performed in any of the ways described herein.

In step 704, the sound processor determines that a stimulation pulse amplitude corresponding to the loudness level is greater than a maximum stimulation pulse amplitude allowed by a compliance voltage associated with a cochlear implant implanted within the patient. Step 704 may be performed in any of the ways described herein.

In step 706, the sound processor directs, in response to the determination, the cochlear implant to represent the loudness level to the patient by directing the cochlear implant to generate and apply one or more stimulation pulses to the patient in accordance with at least one of a first encoding scheme that includes pulse density modulation and a second encoding scheme that includes a combination of pulse amplitude modulation and pulse width modulation. Step 706 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor included in a cochlear implant system associated with a patient, the sound processor comprising:

a processing facility that identifies a loudness level of an audio signal presented to the patient; and a loudness encoding management facility that
determines that a stimulation pulse amplitude corresponding to the loudness level is greater than a maximum stimulation pulse amplitude allowed by a compliance voltage associated with a cochlear implant implanted within the patient, and directs, in response to the determination that the stimulation pulse amplitude is greater than a maximum stimulation pulse amplitude allowed by the compliance voltage, the cochlear implant to represent the loudness level to the patient by directing the cochlear implant to generate and apply a plurality of stimulation pulses to the patient in accordance with a pulse density modulation encoding scheme.

2. The sound processor of claim 1, wherein the loudness encoding management facility directs the cochlear implant patient to represent the loudness level to the patient by generating and applying the plurality of stimulation pulses by way of an electrode disposed within a cochlea of the patient.

3. The sound processor of claim 1, wherein the plurality of stimulation pulses comprises a first stimulation pulse having a first stimulation pulse amplitude and a second stimulation pulse having a second stimulation pulse amplitude, wherein a sum of the first and second stimulation pulse amplitudes is substantially equal to the stimulation pulse amplitude corresponding to the loudness level.

4. The sound processor of claim 3, wherein the loudness encoding management facility directs the cochlear implant to apply the plurality of stimulation pulses to the patient by directing the cochlear implant to sequentially apply the first and second stimulation pulses.

5. The sound processor of claim 4, wherein the pulse density modulation encoding scheme defines a delay time that temporally separates the first and second stimulation pulses.

6. The sound processor of claim 1, wherein the stimulation pulse amplitude corresponding to the loudness level is equal to a stimulation pulse amplitude that a single stimulation pulse must have if the single stimulation pulse is used by the cochlear implant to represent the loudness level to the patient in accordance with a pulse amplitude modulation encoding scheme.

7. The sound processor of claim 1, wherein:
the processing facility identifies an additional loudness level of the audio signal presented to the patient; and
the loudness encoding management facility
determines that an additional stimulation pulse amplitude corresponding to the additional loudness level is less than or equal to the maximum stimulation pulse amplitude allowed by the compliance voltage, and
directs, in response to the determination that the additional stimulation pulse amplitude is less than or equal to the maximum stimulation pulse amplitude allowed by the compliance voltage, the cochlear implant to represent the additional loudness level to the patient by directing the cochlear implant to generate and apply a single stimulation pulse having the additional stimulation pulse amplitude to the patient in accordance with a pulse amplitude modulation encoding scheme.

8. The sound processor of claim 7, wherein:
the plurality of stimulation pulses and the single stimulation pulse are included in a single pulse train applied by way of a single electrode; and the loudness encoding management facility directs the cochlear implant to dynamically switch from operating in accordance with the pulse density modulation encoding scheme to operating in accordance with the pulse amplitude modulation encoding scheme while the single pulse train is being applied by way of the single electrode.

9. The sound processor of claim 1, wherein the loudness encoding management facility directs the cochlear implant to represent the loudness level to the patient without increasing the compliance voltage associated with the cochlear implant.

10. The sound processor of claim 1, wherein the wherein the loudness encoding management facility further directs the cochlear implant to generate and apply the stimulation pulses in accordance with a pulse width modulation encoding scheme.

11. The sound processor of claim 1, wherein:
the processing facility identifies an additional loudness level of the audio signal presented to the patient; and
the loudness encoding management facility
determines that an additional stimulation pulse amplitude corresponding to the additional loudness level is greater than the maximum stimulation pulse amplitude allowed by the compliance voltage and that the additional loudness level cannot be represented using the pulse density modulation encoding scheme, and
increases, in response to the determination that the additional stimulation pulse amplitude is greater than the maximum stimulation pulse amplitude allowed by the compliance voltage and that the additional loudness level cannot be represented using the pulse density modulation encoding scheme, the compliance voltage associated with the cochlear implant.

12. A sound processor included in a cochlear implant system associated with a patient, the sound processor comprising:
at least one processor that
identifies, during a first time slot, a first loudness level of an audio signal presented to the patient,
determines that a first stimulation pulse amplitude corresponding to the first loudness level is less than or equal to a maximum stimulation pulse amplitude allowed by a compliance voltage associated with a cochlear implant implanted within the patient,
directs, in response to the determination that the first stimulation pulse amplitude is less than or equal to the maximum stimulation pulse amplitude applied by the compliance voltage, the cochlear implant to represent the first loudness level to the patient by directing the cochlear implant to generate and apply a single stimulation pulse that has the first stimulation pulse amplitude to the patient in accordance with a pulse amplitude modulation encoding scheme;
identifies, during a second time slot subsequent to the first time slot, second first loudness level of the audio signal presented to the patient,
determines that a second stimulation pulse amplitude corresponding to the second loudness level is greater than the maximum stimulation pulse amplitude allowed by the compliance voltage, and
directs, in response to the determination that the second stimulation pulse amplitude is greater than the maximum stimulation pulse amplitude applied by the compliance voltage, the cochlear implant to represent the second loudness level to the patient by directing the cochlear implant to generate and apply one or more stimulation pulses in accordance with an encoding scheme that is different than the pulse amplitude modulation encoding scheme.

13. The sound processor of claim 12, wherein the encoding scheme that is different than the pulse amplitude modulation scheme includes a pulse density modulation encoding scheme.

14. The sound processor of claim 12, wherein the encoding scheme that is different than the pulse amplitude modulation scheme includes both pulse amplitude modulation and pulse width modulation.

15. The sound processor of claim 14, wherein the at least one processor directs the cochlear implant to generate and apply the one or more stimulation pulses in accordance with the encoding scheme that is different than the pulse amplitude modulation scheme includes both pulse amplitude modulation and pulse width modulation by directing the cochlear implant to generate and apply a second single stimulation pulse that has a stimulation pulse amplitude and a stimulation pulse width that results in the second single stimulation pulse having a total charge corresponding to the second loudness level.

16. The sound processor of claim 12, wherein:
the single stimulation pulse and the one or more stimulation pulses are included in a single pulse train applied by way of a single electrode; and
the at least one processor directs the cochlear implant to dynamically switch from operating in accordance with the pulse amplitude modulation encoding scheme to operating in accordance with the encoding scheme that is different than the pulse amplitude modulation scheme while the single pulse train is being applied by way of the single electrode.

17. A sound processor included in a cochlear implant system associated with a patient, the sound processor comprising:
at least one processor that
identifies a loudness level of an audio signal presented to the patient; and
directs the cochlear implant to encode the loudness level of the audio signal into a plurality of stimulation pulses in accordance with a pulse density modulation encoding scheme.

18. The sound processor of claim 17, wherein the at least one processor directs the cochlear implant to apply the plurality of stimulation pulses to the patient by way of a single electrode.

19. A cochlear implant implanted within a patient and included a cochlear implant system, the cochlear implant comprising:
a receiving facility that receives an instruction from a sound processor included in the cochlear implant system for the cochlear implant to represent a loudness level of an audio signal to the patient;
a loudness encoding management facility that
determines that a stimulation pulse amplitude corresponding to the loudness level is greater than a maximum stimulation pulse amplitude allowed by a compliance voltage associated with the cochlear implant, and
represents, in response to the determination that the stimulation pulse amplitude is greater than a maximum stimulation pulse amplitude allowed by the compliance voltage, the loudness level to the patient by generating and applying one or more stimulation pulses to the patient in accordance with at least one of a first encoding scheme that includes pulse density modulation and a second encoding scheme that includes a combination of pulse amplitude modulation and pulse width modulation.

20. The cochlear implant of claim 19, wherein the loudness encoding management facility represents the loudness level to the patient in accordance with the first encoding scheme by generating and applying a plurality of stimulation pulses by way of an electrode disposed within a cochlea of the patient.

\* \* \* \* \*